United States Patent [19]

Hogan et al.

[11] 4,426,024

[45] Jan. 17, 1984

[54] DEVICE FOR DISPENSING FLUID

[75] Inventors: Lawrence R. Hogan, Lake Villa; Lenart Anderson, Mt. Prospect, both of Ill.

[73] Assignee: Baxter Travenol Laboratories, Inc., Deerfield, Ill.

[21] Appl. No.: 329,706

[22] Filed: Dec. 11, 1981

[51] Int. Cl.³ .......................... A61M 5/00; B67D 5/42
[52] U.S. Cl. ..................................... 222/173; 222/326;
222/334; 222/389; 604/141
[58] Field of Search ............... 222/389, 387, 334, 309,
222/327, 326, 173; 604/141, 143, 147, 152, 410,
411, 414, 407, 232, 154, 155, 187, 208–210, 225

[56] References Cited

U.S. PATENT DOCUMENTS

| | | | |
|---|---|---|---|
| 2,692,706 | 10/1954 | Wiksten | 222/389 |
| 3,353,537 | 11/1967 | Knox et al. | 222/334 |
| 3,395,704 | 8/1968 | Frey et al. | 222/334 |
| 3,799,406 | 3/1974 | St. John et al. | 222/309 |
| 3,993,064 | 11/1976 | McCarthy et al. | 604/224 |

Primary Examiner—Joseph J. Rolla
Assistant Examiner—Thomas Fitzgerald
Attorney, Agent, or Firm—Robert A. Benziger; Paul C. Flattery; George H. Gerstman

[57] ABSTRACT

The fluid dispensing device (10) is utilized in a fluid dispensing system (12) which includes a syringe (22) having a cylindrical barrel (36) with an inlet/outlet opening (20) at a forward end thereof and which is open at the rearward end thereof. A plunger (38) is received in the barrel (36). A source (14) of medicinal additive is coupled by a two-way check valve (18) to the inlet/outlet opening (20). A needle (24) is mounted to the outlet (26) of the valve (18).

The fluid dispensing device (10) is manipulatable to operate the syringe (22), first to draw a precise amount of medicinal additive into the syringe (22) through the valve (18) and second to dispense the precise amount of medicinal additive from the syringe (22) through the needle (24) into, for example, a receptacle (34) having a base liquid therein. The device (10) comprises a body (50), holder (52, 54, 56) on body (50) for receiving and holding the syringe (22), actuator (84) on the body (50) for engaging the plunger (38) and powered piston assembly (88, 90, 92, 98 and 100) for selectively moving the actuator (84) between a forward position where the syringe (22) is ready to draw in a medicinal additive and a rearward portion defining the precise amount of medicinal additive to be drawn into the syringe (22).

5 Claims, 5 Drawing Figures

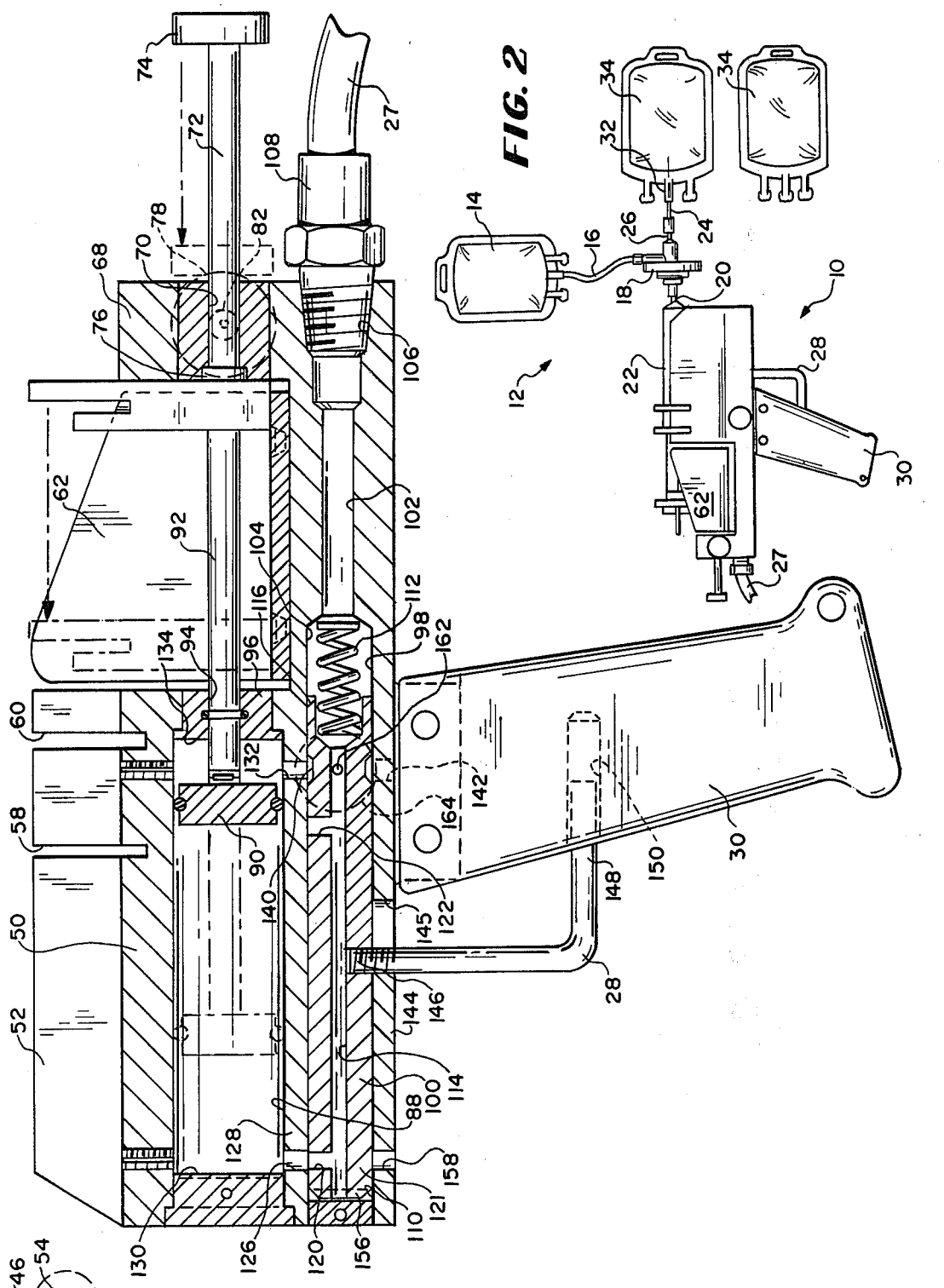

DEVICE FOR DISPENSING FLUID

TECHNICAL FIELD

The present invention relates to a device for dispensing a precise amount of medicinal additive and more specifically for dispensing same from a conventional syringe.

BACKGROUND ART

In the practice of hospital pharmacy it often is necessary to add aseptically to bags, containers, receptacles, etc. of a base liquid such as sterile water, saline solution, dextrose, etc., a medicinal additive such as an antibiotic, a chemotherapeutic agent, an anticoagulant (i.e., heparin) etc., to the liquid. Such additives usually are added by a pharmacist to the base liquid at a pharmacy, and, in a hospital pharmacy, usually are done in batches, e.g., thirty (30) containers at a time are filled with the additive.

This procedure commonly is termed an admixture and usually is done with a syringe. The usual procedure requires the pharmacist to insert the needle of the syringe into a container of the additive, pull back the plunger a precise predetermined distance, withdraw the needle from the additive container, insert the needle into a container of base liquid such as through a resealable port in a plastic bag, and depress the plunger to insert the additive into the container of base liquid followed by removing the needle from the container. This procedure is then repeated a number of times.

In addition to being subject to human error in pulling the plunger back the right distance each time, and in transferring the additive without substantial loss, there also is a strain imposed on the fingers of the operator (pharmacist) in manipulating the syringe, particularly if a large number of these admixtures are being prepared. Such strain and fatigue is known to lead to errors in admixture which result in discarding of the admixture if the error is detected. If the error is undetected, the patient receives inaccurate medication.

Although various syringe devices have been proposed for facilitating the charging of the syringe with a medicinal additive and the dispensing of same, none of these previous attempts at facilitating charging and dispensing have provided the accuracy required as well as relief of strain on the operator while at the same time enabling an operator simply, quickly and accurately to insert precise amounts of medicinal additive into containers of base liquid repetitively.

DISCLOSURE OF INVENTION

The device of the present invention provides a simple and accurate, pressurized fluid-operated device for enabling an operator, such as a pharmacist, simply, quickly and accurately to insert precise amounts of a selected medicinal additive into containers of base liquid repetitively, without error in the amount dispensed and without undue strain on the operator's hand and fingers.

According to the invention there is provided a device for operating a syringe first to draw a precise amount of medicinal additive into the syringe and second to dispense the precise amount of medicinal additive from the syringe, said device comprising a body, holder means on said body for receiving and holding a syringe, actuator means on said body for engaging a plunger of the syringe and powered means for selectively moving said actuator means between a forward position where the syringe is ready to draw in a medicinal additive and a rearward position defining the precise amount of medicinal additive drawn into the syringe, said powered means being operable to move the plunger in a rearward stroke to draw in a precise amount of medicinal additive and to move the plunger in a forward stroke to dispense the precise amount of medicinal additive from the syringe.

Also according to the present invention there is provided a fluid dispensing system including the fluid dispensing device, a syringe, a source of medicinal additive and a two-way check valve having a needle mounted on the outlet therefrom and coupled between the source of medicinal additive and the syringe inlet/outlet.

The device preferably is pneumatically operated and permits an operator using the system to insert into each one of a plurality of containers of base liquid the precise amount (dosage) of medicinal additive.

BRIEF DESCRIPTION OF DRAWINGS

FIG. 2 is a schematic view of the fluid dispensing device showing its use in injecting a medicinal additive into containers of liquid.

FIG. 4 is a front elevational view of the fluid dispensing device shown in FIG. 3 and is taken along line 4—4 of FIG. 3.

FIG. 5 is a sectional view of the fluid dispensing device and is taken along line 5—5 of FIG. 4.

BEST MODE FOR CARRYING OUT THE INVENTION

Figure 1:
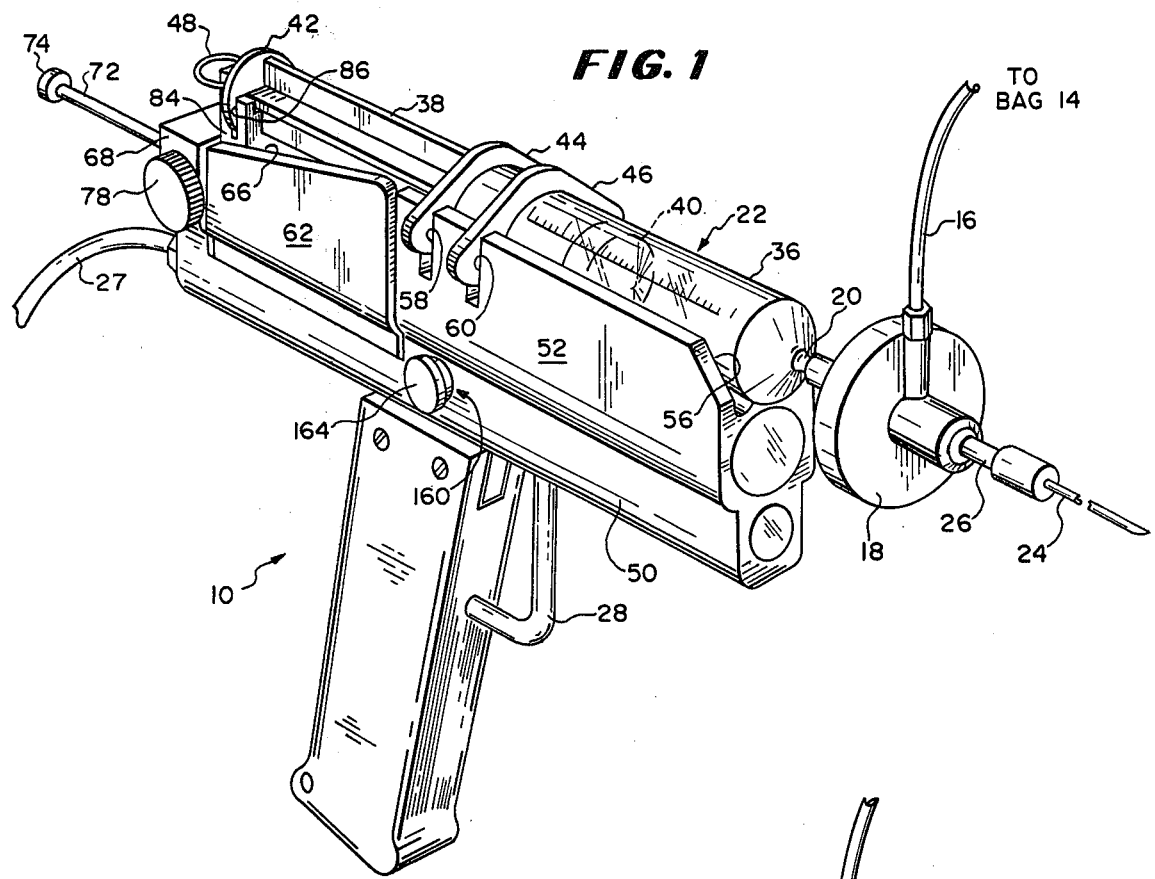
FIG. 1 is a perspective view of the fluid dispensing device of the present invention.

Referring now to the drawings in greater detail there is illustrated a fluid dispensing device 10 which is constructed in accordance with the teachings of the present invention and which is utilized in a fluid dispensing system 12 shown in FIG. 2.

The fluid dispensing system 12 of the present invention also includes a source 14 of medication, i.e., container 14, of medicinal additive such as an antibiotic, an anticoagulant, a chemotherapeutic drug, etc. The container 14 is coupled by tubing 16 to a two-way check valve 18 mounted on the inlet/outlet end 20 of a syringe 22. The syringe 22 is received and held on the admixture device 10 and a needle 24 is mounted on an outlet 26 of the two-way check valve 18. The syringe 22, valve 18 and tubing 16 can be of the type sold by Travenol Laboratories, Inc. of Deerfield, Ill. under the name Multiple Admixture Set.

In using the system 12, an operator will place the syringe 22 in the device 10 with the two-way check valve 18 mounted on the end 20 thereof as shown in FIG. 2. The valve 18 is coupled by tubing 16 to container 14 and the needle 24 is mounted on the outlet 26. Also, the device 10 is coupled to a hose 27 leading to a source of pressurized fluid, e.g., air, such that the device 10 is pneumatically powered.

An operator, such as a pharmacist, can grip the device 10 which has a handgun or pistol configuration. Trigger 28 is located on a handle 30 of the device 10. When trigger 28 is in its released position, a precise amount of medicinal additive is drawn into the syringe. The needle 24 is then inserted into a sealable port 32 of a container 34 of a base liquid such as sterile water, saline solution, dextrose, etc. Depressing the trigger 28 causes the plunger of syringe 22 to move forward or to the right relative to this Figure to inject the precise amount of medicinal additive into the container 34. Then the needle 24 is withdrawn and the procedure is repeated to fill another container 34.

Typically, a plurality of such containers 34 are filled at one time, each with the same precise amount of medicinal additive. Two containers 34 representing such plurality of containers are shown in FIG. 2.

Figure 3:
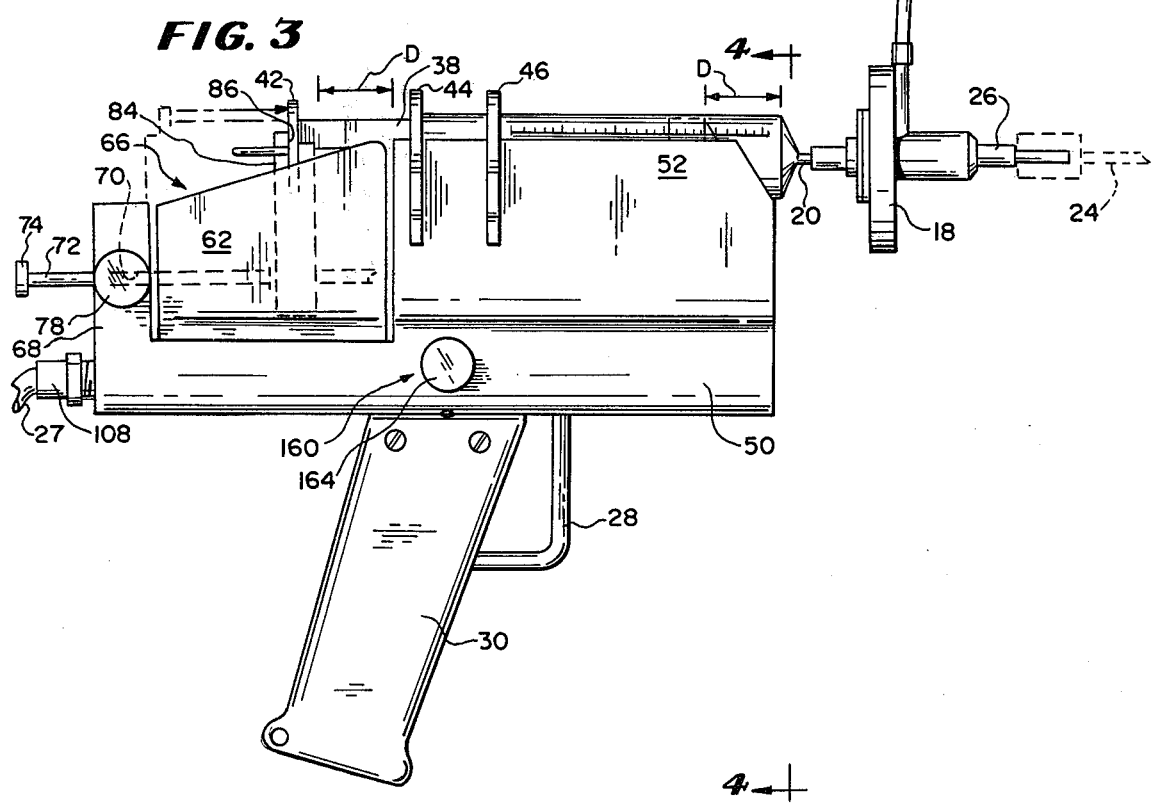
FIG. 3 is a side elevational view of the fluid dispensing device shown in FIG. 1.

As best shown in FIGS. 1 and 3, the syringe 22 includes a transparent cylindrical body 36 having the inlet/outlet end 20 with an opening or port and being open at the opposite end for receiving a plunger 38 in the cylindrical body 36. The plunger 38 has an elastomeric piston 40 on the end thereof within the cylindrical body 36 and an end plate or disc 42 at the outer distal end thereof.

The cylindrical body has conventional scale graduations thereon, e.g., in milliliters or cubic centimeters, for indicating the volume of fluid drawn into the body 36 between the end 20 of the syringe 22 and the front face of the piston 40.

The cylindrical body 36 has, adjacent the open end thereof, a pair of spaced apart flanges 44, 46 extending outwardly from opposite sides of the body 36. These wing-like flanges 44, 46 provide a finger grip formation which permits an operator to insert the first and second fingers of one hand on either side of the cylindrical body 36 between the flanges 44 and 46. A ring 48 is connected to the end disc 42 of the plunger 38 of the syringe 22 for insertion of the thumb of the user for manipulating same.

Referring now to FIGS. 1 and 3, the admixture device 10 has a body 50. The handle 30 is mounted to the underside of the body 50 and extends downwardly therefrom. At the forward end of the body 50 are spaced apart forward side walls 52 and 54 which define therebetween a trough 56 for receiving the syringe 22. Each of the side walls 52 and 54 has a pair of spaced apart slots 58 and 60 which are adapted to receive the wing-like flanges 44 and 46 of syringe 22 therein. In this way the cylindrical body 36 is received and held in place in the trough 56 with the flanges 44 and 46 received in the slots 58 and 60 so as to prevent axial movement of the cylindrical body 36 of the syringe 22. If desired, a restraining strap or means may extend over cylindrical body 36 from side wall 52 to side wall 54 to confine the cylindrical body securely within trough 56.

Behind the trough 56 at the rearward end of the body 50 are two spaced apart rearward side walls 62 which form therebetween a channel 66. The channel 66 extends deeper into the body 50 than the trough 56 and is closed off at the rear end thereof by an end wall 68 which is integral with the body 50.

The rear end wall 68 has a bore 70 therethrough in which is slidably received a rod 72. The outer end of the rod 72 has a knob 74 thereon for facilitating gripping of the rod 72. The inner end of the rod 72 is situated within the channel 66 and has a stop 76 thereon.

The rod 72 and the stop 76 at the inner end thereof are adjustably positionable by means of a thumbscrew 78 which extends through a threaded bore 70 in one side of the end wall 68 such that an inner end 82 of the thumbscrew 78 (as shown in FIG. 5) can be forced against the rod 72 in the bore 70 for holding the rod 72 at a particular position.

Within the channel 66 is positioned an actuator or pusher block 84. The block 84 has a slot 86 in the upper surface thereof which is adapted to receive the end disc or end plate 42 of the plunger 38. Movement of the plunger 38 in and out of the cylindrical body or barrel 36 of the syringe 22 is controlled by movement of the block 84 within the channel 66 and the extent of rearward movement of the block 84 is determined by the position of the stop 76.

Referring now to FIG. 5, it will be apparent that within the body 50 beneath the trough 56 a cylinder 88 is provided. Within this cylinder 88 is positioned a piston 90. A piston rod 92 is connected to the piston 90 and extends through a bore 94 in an end wall 96 of the cylinder 80 for connection to the actuator or pusher block 84. In this way, the actuator or pusher block 84 is moved when the piston 90 is moved, rearwardly or forwardly, within the cylinder 88 in the body 50. Cylinder 88, the piston 90 and piston rod 92 form or define a powered means for moving the block 84 forwardly or rearwardly in a forward stroke or a rearward stroke.

Within the body 50 beneath the cylinder 88 is an elongate cavity 98 in which is received a valve member 100. A passageway 102 within the body 50 communicates a rearward end 104 of the cavity 98 with an inlet port 106 in the body 50 in which is received a fitting 108. Fitting 108 is situated at the end of the hose 27 whereby pressurized fluid, such as air, can be delivered into the body to the cavity 98 and the valve member 100.

As shown in FIG. 5, the valve member 100 is urged toward a closed forward end 110 of the cavity 98 by a spring 112 located at the rearward end 104 of the cavity 98. Spring 112 is confined between the rearward end 104 and the valve member 100.

The valve member 100 has an elongate axial passageway 114 therein which opens at a rearward end 116 of the valve member 100 for communicating with the inlet port 106. The valve member 100 also has a first radial port 120 at a forward end 121 of the valve member 100 and a second radial port 122 at the rearward end 116 of the valve member 100. Both of these radial ports 120, 122 communicate with the axial passageway 114 and are adapted to mate, respectively, with a first orifice 126 extending through a wall 128 of the cylinder 88 at a forward end 130 thereof and a second orifice 132 in the wall 128 at a rearward end 134 of the cylinder 88.

In FIG. 5 it will be apparent that the spring 112 biases the valve member 100 to a forward position thereof where the first radial port 120 is in fluid communication with the first orifice 126. As a result, pressurized air normally is applied through the inlet port 106, pasageway 102, axial passageway 114 in the valve member 100, first radial port 120 and first orifice 126 to the forward end 130 of the cylinder 88 for urging the piston 90 in the cylinder 88 rearwardly thereby to urge actuator or pusher block 84 toward the rearward end of the channel 66 and against the stop 76 at the inner end of the rod 72.

It will be appreciated that when the valve member 100 is in this position, an annular groove 140 in the valve member 100 is in communication with the second orifice 132 and also is in communication with a vent port 142 in a bottom wall 144 of the body 50 so that the rearward end 134 of the cylinder 88 is vented through the second orifice, the annular groove 140 and the vent port 142 to atmosphere.

The trigger 28 is in the form of an L shaped rod which extends through a slot 145 in the bottom wall 144 and is fixed at one end 146 to the valve member 100. The other end 148 is received in a bore 150 in the handle 30.

In operating the device 10 and more particularly the valve member 100 thereof, the trigger 28 is squeezed to push it rearwardly in the slot 145 and bore 150 thereby to move the valve member 100 rearwardly to bring the second radial port 122 into registry with the second orifice 132. At the same time, a beveled forward end 156 of the valve member 100 registers with the first orifice 126 and another vent port 158 in the bottom wall 144 so that while the trigger 28 is depressed, pressurized air is supplied from the inlet port 106 to the axial passageway 114, the second radial port 122 and the second orifice 132 to the rearward end 134 of the cylinder 88 thereby to urge this piston 90 forwardly to the forward position thereof. At the same time, the forward end 130 of the cylinder 88 is vented through the first orifice 126 around the beveled front end 156 of the valve member 100 and through the vent port 158.

When operating the device 10, the force on the piston 90 by the pressurized air could be such as to cause improper functioning of the filling of the syringe 22 with fluid or the ejection of fluid from the syringe 22. For example, if the trigger 28 is pulled back too fast, air bubbles can be drawn into the syringe barrel 36. To alleviate this potential misfunction in the charging or filling of the syringe 22 and the dispensing of medicinal additive therefrom, a throttling valve 160 is provided in the form of a screw 162 having a finger manipulatable thumbwheel 164. The end of the screw 162 which is adapted to extend into the axial passageway 114 within the valve member 100 is shown in FIG. 5. Thus, in controlling or throttling the operation of the device 10 an operator will rotate the thumbwheeel 164 to adjust the extent to which the end of the screw 162 extends into the axial passageway 114 to throttle inlet air pressure.

It will be apparent from the foregoing description that the fluid dispensing device 10 and the system 12 with which it is utilized provide a very simple, quick and accurate mechanism for repetitively drawing in or filling a portion of the cylindrical body or barrel 36 of the syringe 22 with a precise amount (dosage) of medicinal additive and then dispensing such precise amount of medicinal additive into a container 34 of base liquid. In this respect, it will be noted from FIG. 3 that each time the trigger 28 is released, the piston 40 will be urged rearwardly within the barrel 36 a distance D which is equivalent to a certain volume of liquid that is drawn into the barrel 36 of the syringe 22. This distance D, of course, also is equal to the distance that the pusher block 84 moves from the forward end of the channel 66 to and against the stop 76 at the end of the rod 72. This distance D can be adjusted as desired merely by manipulating the thumbscrew 78 and adjusting the position of the stop 76 by sliding the rod 72 within the bore 70.

Of course, when the trigger 28 is depressed, the plunger 38, and more particularly the piston 40 at the inner end thereof, is urged forwardly to eject the volume of medicinal additive at the front end of the barrel 36 of the syringe 22 through the two-way check valve 18 and the needle 24 into a receptacle, such as the container 34.

The dispensing device 10 and the system 12 with which it is used permit an operator, such as a hospital pharmacist, accurately and precisely to charge or fill the syringe 22 with a desired amount of medicinal additive and then to inject that amount of medicinal additive into a container 34 of a base liquid with minimal strain on the operator. In this respect, once the stop 76 is fixed in a desired position, the operator does not need to monitor the extent to which the piston 40 of the plunger 38 is pulled out of the barrel 36 of the syringe 22. Also strain on the fingers and thumb of the operator is eliminated since he does not have to grip the syringe 22 with his first and second fingers and thumb. Instead, he merely grips the trigger 28 in the manner described above.

Since compressed air is readily available in most hospital pharmacies, the fluid dispensing device 10 can be easily utilized by a pharmacist without the need for obtaining a source of pressurized air. Moreover, the dispensing device 10 is hand portable and similar in size to, while being lighter in weight than, an electric drill.

The adjustable stop 76 permits the fluid dispensing device 10 to be semi-automatic thereby to give consistent fluid amounts as selected. Typically a 22 cc syringe is snapped into the trough 56 at the top of the body 50 and the adjustable stop 76 at the end of the rod 72 is positioned at the number of cc's desired. The air connection is then made and the pressure is adjusted by means of throttling valve 160 to the pressure desired. When the trigger 28 is not squeezed, the syringe 22 is in the extended or full position. Then squeezing of the trigger 28 moves the plunger forward emptying the syringe 22.

If desired, a counter can be mounted on the side of the body 50 to "count" the number of strokes of the plunger 38 in order to not loose track of the total cc's dispensed in numerous fill cycles.

Also, although the fluid dispensing device 10 is shown in a preferred fluid dispensing system 12, it is to be appreciated that the filling and dispensing of fluid from a syringe 22 mounted in the fluid dispensing device 10 can be accomplished in many different ways and without the utilization of the two-way check valve 18. In such use of the dispenser 10 with a syringe 22, the needle 24 is connected directly to the inlet/outlet 20 of the syringe 22.

It will be apparent from the foregoing description that the dispensing device 10 of the present invention and fluid dispensing system 12 utilizing same have a number of advantages, some of which have been described above and others of which are inherent in the invention. Also it will be appreciated that modifications can be made to the fluid dispensing device 10 without departing from the teachings of the invention. Accordingly, the scope of the invention is only to be limited as necessitated by the accompanying claims.

We claim:

1. A device for operating a syringe, first to draw a precise amount of medicinal additive into the syringe and second to dispense the precise amount of medicinal additive from the syringe, said device comprising:

a body having spaced apart forward sidewalls defining a trough therebetween for receiving the syringe, each sidewall having a pair of slots therein aligned with the slots in the other sidewall for receiving finger grip flanges extending outwardly from the syringe, and trough and said slot defining said means for receiving and holding the syringe, said body having spaced apart rearward walls for defining a channel therebetween, said channel being deeper than said trough and the rear of said trough opening onto said channel, said body further having a rear wall defining the rear end of said channel;

holder means on said body for receiving and holding a syringe;

actuator means on said body for engaging a plunger of the syringe, said actuator means including a pusher block in said channel with means thereon for engaging the distal end of the plunger; and, powered means selectively moving said actuator means between a forward position where the syringe is ready to draw in a medicinal additive and a rearward position defining the precise amount of medicinal additive to be drawn into the syringe, said powered means thereby being operable to move the plunger in a rearward stroke to draw in a precise amount of medicinal additive and to move the plunger in a forward stroke to dispense the precise amount of medicinal additive from the syringe.

2. The device according to claim 1 wherein said body has a cylinder therein beneath said trough, a piston being situated in and movable in said cylinder and a piston rod extending from the end of said cylinder adjacent said channel and being connected to and between said piston and said pusher block, said piston and cylinder defining said powered means.

3. The device according to claim 2 wherein said body has a cavity therein beneath said cylinder and said powered means includes a movable valve member in said cavity, the respective ends of said cylinder being in communication with respective ends of said cavity, said body further having an inlet port for connection to a source of pressurized fluid and wherein trigger means are mounted on said body and coupled to said valve member for enabling an operator to move said valve member to cause movement of said piston in said cylinder to move said pusher block thereby to move the plunger in a direction into or out of the syringe.

4. The device according to claim 2 wherein said end wall has a bore therethrough, a rod being slidably received in the bore, the inner end of said rod defining a stop for limiting rearward movement of said pusher block in said channel, and means provided for releasably locking said rod in said bore at a desired position of the stop defining inner end thereof.

5. A device for operating a syringe, first to draw a precise amount of medicinal additive into the syringe and second to dispense the precise amount of medicinal additive from the syringe, said device comprising:

a body having an inlet port for communication with a source of pressurized fluid;

holder means on said body for receiving and holding a syringe;

actuator means on said body for engaging a plunger of the syringe;

powered means which includes a double-acting piston mounted in a cylinder formed in said body, said body having passage means communicating said inlet port with the ends of said cylinder of said powered means, and a piston rod connected between said piston and said actuator means, said powered means selectively moving said actuator means between a forward position where the syringe is ready to draw in a medicinal additive and a rearward position defining the precise amount of medicinal additive to be drawn into the syringe, said powered means thereby being operable to move the plunger in a rearward stroke to draw in a precise amount of medicinal additive and to move the plunger in a forward stroke to dispense the precise amount of medicinal additive from the syringe;

valve means included in said powered means for selectively venting one end of said cylinder while at the same time communicating the other end of said cylinder to said inlet port; said valve means including an elongated valve member mounted in a cavity in said body and being movable between a first position and a second position, said cavity extending parallel to said cylinder, said body having a first orifice between one end of said cylinder and said cavity and a second orifice between the other end of said cylinder and said cavity, said valve means having an axial passageway therein which is open at one end to said inlet port, a first radial port which extends from said axial passageway to the periphery of said valve member and which is normally in communication with said first orifice at said first position of said valve member, and a second radial port which extends from said axial passageway to the periphery of said valve member and which is adapted to mate with said second radial port in said second position of said valve member, spring means in said cavity adjacent said inlet port for urging said valve member to said first position, said body and said valve means having vent means for venting said first or second orifice when said second or first radial port is in communication with said second or first orifice; and, trigger means connected to said valve means and operable upon depression thereof to move said valve member against said spring means to said second position thereof.

* * * * *